United States Patent [19]

Nickolson

[11] 4,089,852
[45] May 16, 1978

[54] PROCESS FOR THE PREPARATION OF 21-HYDROXY-16-PREGNEN-20-ONE DERIVATIVES

[75] Inventor: Robert Nickolson, Berlin, Germany

[73] Assignee: Schering Aktiengesellschaft, Berlin and Bergkamen, Germany

[21] Appl. No.: 682,967

[22] Filed: May 4, 1976

[30] Foreign Application Priority Data

May 9, 1975 Germany ............................. 2521231

[51] Int. Cl.$^2$ ............................................. C07J 17/00
[52] U.S. Cl. .................. 260/239.55 R; 260/239.55 C; 260/239.55 D; 260/397.47; 260/397.5; 260/397.45
[58] Field of Search ......................................
/Machine Searched Steroids; 260/397.5, 239.55

[56] References Cited

U.S. PATENT DOCUMENTS 3,793,350  2/1974  Crabbe ........................... 260/397.45

Primary Examiner—Elbert L. Roberts
Attorney, Agent, or Firm—Millen & White

[57] ABSTRACT

$\Delta^{16}$-21-hydroxy-20-keto steroids of the pregnane series having an otherwise unsubstituted D-ring and a 13-methyl or -ethyl group, and 21-ethers and -esters thereof, are produced by reaction of a corresponding D-ring saturated 17-keto steroid with a lithium compound of the formula

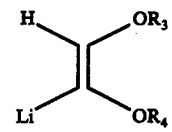

thereby converting the 17-keto group to a 17$\beta$-hydroxy-20$\alpha$-enol ether in which the 17$\alpha$-side chain has the formula

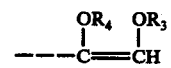

wherein $R_3$ and $R_4$ have the values given above, and, in any desired sequence, splitting off $R_3$ and/or $R_4$ enol ether by hydrolysis; eliminating 17$\beta$-hydroxy group, preferably after acylation, with formation of a $\Delta^{16}$-double bond; and, if desired, splitting off any blocking group.

9 Claims, No Drawings

PROCESS FOR THE PREPARATION OF 21-HYDROXY-16-PREGNEN-20-ONE DERIVATIVES

BACKGROUND OF THE INVENTION

This invention relates to a process for the production of 21-hydroxy-16-pregnen-20-one compounds. The process of this invention is simpler on a technical scale than conventional methods for preparing 21-hydroxy-16-pregnen-20-one derivatives of Formula II, as set forth in DAS (German Published Application) 2,154,382.

SUMMARY OF THE INVENTION

In a process aspect, this invention relates to a method of preparing $\Delta^{16}$-21-hydroxy-20-keto steroids of the pregnane series having a 13-methyl or -ethyl group and an otherwise unsubstituted D-ring, and 21-ethers thereof, comprising the steps of (a) condensing a corresponding 17-keto steroid containing no other free keto function with a lithium compound of the formula

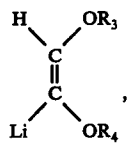

wherein $R_3$ and $R_4$ each are alkyl of 1–4 carbon atoms or collectively are alkylene or alkylidene of 1–3 carbons in the alkylene or alkylidene chain and up to 6 carbon atoms in the alkylene or alkylidene, thereby converting the 17-keto group to a 17$\beta$-hydroxy-20$\alpha$-enol ether in which the 17$\alpha$-side chain has the formula

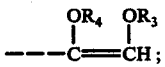

and, in either order, (b) hydrolyzing at least the $OR_4$ group of the enol ether thus-produced to form a 20-keto-21-oxy side chain and eliminating the 17$\beta$-OH to form a $\Delta^{16}$-double bond.

In a composition aspect, this invention relates to novel 17$\beta$-hydroxy-20$\alpha$-enol ethers of the pregnane steroids produced as intermediates in the process of this invention.

DETAILED DISCUSSION

In a preferred embodiment, this invention relates to a process for the preparation of 21-hydroxy-16-pregnen-20-one compounds of Formula I

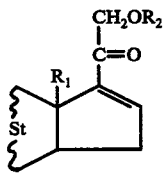

wherein
$R_1$ is methyl or ethyl,
$R_2$ is hydrogen, lower alkyl, hydroxy lower alkyl or lower alkanoyl; and
St is the remainder of the ABC ring system of a 19-norpregnane which has 1–4 double bonds and is optionally substituted in the 6- and/or 10-position by methyl and/or in the 3- and/or 11-position by hydroxy, lower alkoxy, lower acyloxy, nitriloxy, oxo, lower alkylenedioxy, or phenylenedioxy;
comprising the step of condensing a 17-keto steroid of Formula II

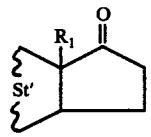

wherein
$R_1$ is as above and
St' is the remainder of the ABC ring system of a 19-nor-pregnane which is saturated or has 1–4 double bonds and is optionally substituted in the 6- and/or 10-position by methyl and/or in the 3- and/or 11-position by hydroxy, lower alkoxy, lower acyloxy, nitriloxy, lower trialkylsilyloxy, tetrahydropyranyloxy, lower alkylenedioxy or phenylenedioxy;
with a lithium compound of Formula III

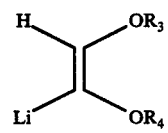

wherein $R_3$ and $R_4$ each are lower alkyl or collectively are lower alkylene or alkylidene;
to form a compound of Formula IV

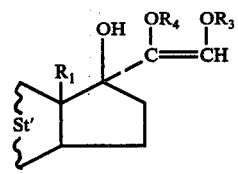

wherein St', $R_1$, $R_3$ and $R_4$ are as above;
and, in any desired sequence, splitting off $R_3$ and/or $R_4$ enol ether by hydrolysis; eliminating the 17$\beta$-hydroxy group, preferably after acylation, with formation of a $\Delta^{16}$-double bond; and, if desired, splitting off any blocking group.

Alkoxy optionally present in the 3- and/or 11-position of St' is preferably of 1–6 carbon atoms. Suitable alkoxy are, for example, methoxy, ethoxy, propoxy, isopropoxy, butoxy, isobutoxy and tert.-butoxy.

Acyloxy optionally present in the 3- and/or 11-position of St' is preferably of 1–6 carbon atoms in the alkanoyl residue. Suitable alkanoyloxy are, for example, formyloxy, acetoxy, propionyloxy, butyryloxy, trimethylacetoxy, tert.-butylacetoxy, pentanoyloxy and hexanoyloxy.

A lower trialkylsilyloxy substituent in St' is preferably one of three identical alkyl of 1–4 carbon atoms. Especially preferred is trimethylsilyloxy.

Lower alkylenedioxy or alkylidenedioxy optionally present in the 3- or 11-position of St or St' is preferably of 2–6 carbon atoms in the alkylene, most preferably of 2–3 carbon atoms in the alkylene, which forms a ring with the $C_3$ or $C_{11}$ carbon and two oxygen atoms. Suitable residues are, for example, ethylenedioxy, 1,3-propylenedioxy, 2-methyl-1,3-propylenedioxy and 2,2-dimethylpropylidenedioxy.

In conducting the process of this invention, the aforementioned groups can be located, as set forth specifically, in the 3- and/or 11-positions of the residue St' or in any other position. However, only products of Formula I, that is, compounds substituted at $C_3$- and $C_{11}$- are presently of commercial significance.

If St' has free β-hydroxy in the 3-position, St' can optionally have additional double bonds in the 5(6)- or 5(10)- and/or 9(11)-positions.

If St' has an esterified or etherified hydroxy, as described above, in the 3-position, it can have additional double bonds in the 1,3,5(10)- and/or 9(11)-positions or in the 2,5-(10)- and/or 9(11)-positions or in the 3- and-/or 5- and/or 9(11)-positions.

If St' has a ketalized oxo in the 3-position, it can have additional double bonds in the 5(6)- and/or 5(10)- and-/or 9(11)-positions.

If there is no double bond at the 10-position of St', there is hydrogen or methyl in the 10β-position.

St means the above residues, particularly the remainder of the ABC ring system of a 19-nor-pregnane which is saturated or has an oxo substituent in the 3- and/or 11-positions and is optionally substituted in the 6- and-/or 10-positions by methyl.

$R_2$ is preferably alkanoyl of 1–6 carbon atoms, e.g., formyl, acetyl, propionyl and butyryl.

$R_3$ and $R_4$ each are lower alkyl, preferably of 1–4 carbon atoms, such as methyl, ethyl, propyl and butyl, or collectively are alkylene, preferably alkylidene of 1–6 carbon atoms. Alkylene or alkylidene are, for example, methylene, ethylene, ethylidene, 1,3-propylene, 1,1-propylidene, 2,2-propylidene, 1,1-butylidene, 2,2-butylidene, 2-methyl-1,3-propylidene and 2,2-dimethylpropylidene.

Hydroxy-substituted lower alkyl $R_2$ means a group otherwise identical to lower alkyl residue $R_3$ or which is formed from an alkylene $R_3$ and $R_4$ by hydrolysis of the —$OR_4$ linkage.

The first step of the process of this invention is preferably conducted as follows:

A solution of a lithium compound of Formula III is prepared by reacting a compound of Formula V

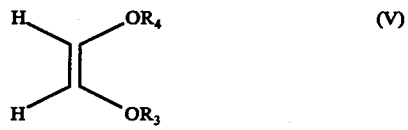

(V)

wherein $R_3$ and $R_4$ are as above, in an inert solvent with an alkyl lithium compound and treating the thus-obtained solution with a 17-keto steroid of Formula II.

Preferred alkyl lithium compounds are those wherein alkyl are of 1–8 carbon atoms, for example, butyllithium, sec.-butyllithium, more preferably, tert.-butyllithium or tert.-amyllithium.

Suitable insert solvents for this reaction step are, for example, hydrocarbons such as pentane, hexane, cyclohexane, benzene and toluene; ethers such as diethyl ether, diisopropyl ether, dibutyl ether, glycol dimethyl ether, dioxane and tetrahydrofuran; dipolar aprotic solvents such as dimethylformamide or hexamethylphosphoric triamide; tertiary amines such as trimethylamine, N-methylmorpholine and N, N, N, N-tetramethylethylenediamine; or mixtures thereof.

The first step of the process of this invention is preferably conducted as a temperature of −80° to +50° C.

The first step of the process of this invention gives compounds of Formula IV in surprisingly good yields.

Compounds of Formula IV are converted to steroids of Formula I by, in any desired sequence, splitting off enol ether $R_3$ and/or $R_4$ by hydrolysis and eliminating the 17β-hydroxy, preferably after acylation, with formation of a $\Delta^{16}$-double bond.

Hydrolytic cleavage of enol ether groups $R_3$ and/or $R_4$ is done under conditions customarily employed for cleavage of enol ethers. For example, enol ethers are reacted in an inert aqueous solvent with a mineral acid such as hydrochloric acid, sulfuric acid, phosphoric acid or perchloric acid; a sulfonic acid such as methanesulfonic acid or p-toluenesulfonic acid; or a strongly acidic carboxylic acid such as oxalic acid or trifluoroacetic acid at a reaction temperature of 0° C, to 150° C., preferably at 50°–120° C.

Suitable inert solvents for this reaction step are, for example, lower alcohols such as methanol, ethanol and isopropanol; polar ethers such as dioxane, tetrahydrofuran, glycol monomethyl ether or glycol dimethyl ether; dipolar aprotic solvents such as dimethylformamide, N-methylpyrrolidone, N-methylacetamide or hexamethylphosphoric triamide; lower carboxylic acids, for example, formic acid or acetic acid; or mixtures of these solvents.

The corresponding 20-oxo compounds are produced in surprisingly high yields by the hydrolysis. However, depending on the structure of the starting compound of Formula IV, minor amounts of isomeric 21-oxo compounds can be formed. These can be isomerized to the desired 20-oxo compounds by heating in pyridine, lutidine or collidine.

During the hydrolysis, it is also possible to cleave by hydrolysis any enol ether, trialkylsilyloxy, ketal, tert.-butoxy, tetrahydropyranoyloxy and ester blocking groups present in St' and to isomerize any double bonds in a conventional manner.

Depending on the hydrolysis conditions selected and the structure of $R_3$, the 21-ether bond can be retained during the hydrolysis. If complete hydrolysis of this bond is intended, it is advantageous to use compounds of Formula III wherein $R_3$ and $R_4$ collectively are alkylidenedioxy as starting materials. On the other hand, it is frequently expedient to acylate, before cleaving both enol ethers $R_3$ and $R_4$, the compounds to attain simultaneous exchange of ether $R_3$ and elimination of the acylated 17β-hydroxy with formation of a $\Delta^{16}$-double bond.

For elimination of the 17β-hydroxy, methods conventionally employed for elimination of 17α-hydroxy of 17α-hydroxypregnan-20-one derivatives can be used.

Preferably, the elimination is conducted by acylating the 17β-hydroxy compound and eliminating 17β-acyloxy.

Methods customarily utilized for the acylation of tertiary hydroxy groups can be used to acylate the compounds. Preferably, the acylation is carried out by reacting the compounds in an inert solvent with a corresponding acid chloride, acid anhydride, or mixed acid anhydride, e.g., a mixed anhydride of a carboxylic acid with trifluoroacetic acid, methanesulfonic acid, or p-toluenesulfonic acid, in the presence of a mineral acid such as hydrogen chloride, sulfuric acid or perchloric acid; a sulfonic acid, e.g., methanesulfonic acid or p-toluenesulfonic acid; of a strongly acidic carboxylic acid, e.g., trifluoroacetic acid; or of p-dimethylaminopyridine. Preferred acid chlorides or acid anhydrides for the acylation are those derived from alkanecarboxylic acids of 1–6 carbon atoms, e.g., formic acid, acetic acid, propionic acid and butyric acid. Suitable acid chlorides or acid anhydrides include, for example, acetic-formic anhydride, acetyl chloride, acetic anhydride, acetic-p-toluenesulfonic anhydride, acetic-trifluoroacetic anhydride, propionyl chloride and butyryl chloride.

Suitable inert solvents for this reaction are, for example, hydrocarbons, e.g., benzene, toluene or xylene; chlorinated hydrocarbons such as methylene chloride, chloroform, tetrachloromethane, tetrachloroethane, or chlorobenzene; ethers such as diethyl ether, dibutyl ether, dioxane, tetrahydrofuran or glycol dimethyl ether; dipolar aprotic solvents such as acetonitrile, dimethylformamide, N-methylpyrrolidone or hexamethylphosphoric triamide; the acid chlorides or acid anhydrides themselves, or corresponding carboxylic acids; and mixtures thereof.

Acylation with simultaneous exchange of $-OR_3$ can be accomplished, if desired, by conducting the acylation in the presence of carboxylic-p-toluenesulfonic anhydrides and/or the presence of Lewis acids, for example, boron trifluoride etherate, boron trichloride, boron tribromide, iron (III) chloride, titanium (IV) chloride or zinc chloride.

During acylation, any remaining free hydroxy groups, e.g., the 21-hydroxy, are acylated along with the 17β-hydroxy.

Subsequent cleavage of 17β-acyloxy to form $\Delta^{16}$-steroids likewise takes place according to conventional methods. A preferred method is, for example, reaction of the compounds with alkali metal salts of lower carboxylic acids, e.g., sodium acetate or preferably potassium acetate, in a dipolar aprotic solvent, such as dimethylformamide, N-methylpyrrolidone or hexamethylphosphoric triamide, at a temperature of about 20° to 150° C.

After the cleavage step, any acyloxy groups remaining in the steroid can be split off either by the foregoing hydrolysis method or by treatment with a base in a conventional manner. Saponification methods include, for example, saponification with alcoholic alkali metal alkanolate solutions, for example, sodium methylate or sodium ethylate solution; or saponification with aqueous alkali metal hydroxide, alkali metal carbonate or alkali metal bicarbonate solution, e.g., potassium hydroxide, potassium carbonate, potassium bicarbonate, sodium hydroxide or sodium carbonate solution, in the presence of lower alcohols, dipolar aprotic solvents or chlorinated hydrocarbons such as methylene chloride or chloroform.

21-Hydroxy-16-pregnen-20-one derivatives of Formula I are valuable intermediates for the preparation of pharmacologically effective steroids, including hydrocortisone, desoxycorticosterone and derivatives thereof.

The following examples serve for explaining the process of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

(a) A solution of 10.0 ml. of absolute pentane, 10.0 ml. of absolute tetrahydrofuran, and 0.9 ml. of dimethoxyethylene is cooled to −35° C. and 4 ml. of a 2-molar solution of tert.-butyllithium in hexane is added dropwise thereto under an argon atmosphere within 5 minutes. The mixture is stirred for 10 minutes at −20° C. and combined with a solution of 400 mg. of 3-(2′-tetrahydropyranoyloxy)-5-androsten-17-one in 5 ml. of absolute tetrahydrofuran. The reaction mixture is agitated for another 10 minutes and poured into ice-cold, dilute aqueous ammonium chloride solution. The reaction mixture is extracted with ethyl acetate; the ethyl acetate phase is washed, dried over sodium sulfate, concentrated under vacuum, and the product is 360 mg. of 20,21-dimethoxy-3-(2′-tetrahydropyranyloxy)-17α-pregna-5,20-dion-17β-ol as a crude compound.

The crude product can be purified by recrystallization from ether. Melting point of the pure product: 173.5° – 174° C.

(b) A solution of 350 mg. of 20,21-dimethoxy-3-(2′-tetrahydropyranyloxy)-17α-pregna-5,20-dion-17β-ol in 10 ml. of tetrahydrofuran is combined with 2.0 ml. of 1N HCl and heated for 2 hours to 50° C. The mixture is allowed to cool down and then combined with aqueous sodium bicarbonate solution, whereafter it is extracted with methylene chloride; the methylene chloride phase is washed, dried, and concentrated under vacuum, thus obtaining 320 mg. of 3β,17α-dihydroxy-21-methoxy-17α-pregn-5-en-20-one as a crude product which melts, after recrystallization from acetone-hexane, at 164°–165° C.

(c) 250 mg. of 3β,17α-dihydroxy-21-methoxy-17α-pregn-5-en-20 -one is dissolved in 5.0 ml. of acetic acid and 3.5 ml. of acetic anhydride, combined with 0.01 ml. of 70% perchloric acid, and dissolved for 20 minutes at room temperature. The reaction mixture is combined with water, extracted with methylene chloride; the methylene chloride phase is washed and concentrated under vacuum, thus obtaining 210 mg. of 3β,17α-diacetoxy-2-methoxy-17α-pregn-5-en-20-one as a crude product. The latter is dissolved without further purification in 4.0 ml. of dimethylformamide, combined with 350 mg. of anhydrous potassium acetate, and heated under argon for 6 hours to 105° C. The mixture is then poured into ice water, extracted with ethyl acetate; the ethyl acetate phase is washed, dried over sodium sulfate, concentrated under vacuum; and the residue is chromatographed by means of a hexane-acetone gradient over a silica gel column, thus producing 3β-acetoxy-21-methoxy-5,16-pregnadien-20-one, m.p. 123° – 126.5° C. (from acetone-hexane).

EXAMPLE 2

(a) 800 mg. of 1,3-dioxole is dissolved in 25 ml. of absolute tetrahydrofuran; the mixture is cooled to −40° C. and a 2.0-molar solution of tert.-butyllithium is 3.5 ml. of pentane is added dropwise to the reaction mixture under argon; and the mixture is stirred for 10 minutes at −30° C. Thereafter, the mixture is combined with 500 mg. of a solution of 3,3-ethylenedioxy-5(10)-estren-17-one in 8.0 ml. of absolute tetrahydrofuran, and the mixture is stirred for 30 minutes at −20° C. and then carefully acidified with 2.5 ml. of 4N hydrochloric acid, whereafter it is heated for 3 hours to 50° C. The reaction mixture is then neutralized with aqueous sodium bicarbonate solution, extracted with ethyl acetate; and the ethyl acetate extract is washed, dried, concentrated under vacuum; and the yield is 435 mg. of 17β,21-dihydroxy-19-nor-17α-pregn-4-ene-3,20-dione as the crude product which melts, after purification over a silica gel column with an acetone-hexane gradient, at 155°–157° C.

(b) 400 mg. of 17β,21-dihydroxy-19-nor-17α-pregn-4-ene-3,20-dione is combined with 6.0 ml. of glacial acetic acid, 3.0 ml. of acetic anhydride, and 0.01 ml. of 70% perchloric acid and stored for 30 minutes at room temperature. The mixture is then diluted with 20 ml. of methanol, combined with 4.0 ml. of dilute hydrochloric acid, and heated for 5 minutes under reflux. The cooled reaction mixture is combined with water, extracted with chloroform, and the chloroform extract is washed, dried, and concentrated under vacuum, thus obtaining 345 mg. of 17β,21-diacetoxy-19-nor-17α-pregn-4-ene-3,20-dione as a crude product.

The crude product is combined without further purification with 6.0 ml. of dimethylformamide and 450 mg. of anhydrous potassium acetate and heated for 8 hours to 105° C. The reaction mixture is worked up as described in Example 1(b), yielding 280 mg. of 21-acetoxy-19-nor-4,16-pregnadiene-3,20-dione which melts, after recrystallization from acetone-hexane, at 167°–170° C.

EXAMPLE 3

(a) Under the conditions of Example 2(a), 750 mg. of 2,2-dimethyldioxole is reacted with 400 mg. of 3,3-ethylenedioxy-5-androsten-17-one and then worked up, thus obtaining 310 mg. of 17β,21-dihydroxy-17α-pregn-4-ene-3,20-dione as the crude product.

(b) The crude product is reacted and worked up without any further purification as described in Example 2(b), and chromatography of the crude product over a silica gel column yields the 21-acetoxy-4,16-pregnadiene-3,20-dione, m.p. 153°–154° C.

EXAMPLE 4

(a) Under the conditions of Example 2(a), 800 mg. of 1,4-dioxene is reacted with 500 mg. of 3,3-ethylenedioxy-5-androsten-17-one and worked up, thus obtaining 390 mg. of 17β-hydroxy-21-(2'-hydroxyethoxy)-17α-pregn-4-ene-3,20-dione as the crude product.

(b) This crude product is combined, without further purification, with 20 ml. of methylene chloride, 3.0 ml. of acetic anhydride, and 50 mg. of boron trifluoride etherate (dissolved in 1 ml. of methylene chloride) and kept for 6 hours at room temperature. The mixture is then poured into ice water and extracted with chloroform. The chloroform phase is washed, dried, and concentrated under vacuum. The thus-obtained crude product is dissolved in 4.0 ml. of dimethylformamide, combined with 350 mg. of anhydrous potassium acetate, and heated for 6 hours to 105° C. The reaction mixture is worked up as described in Example 3(b), thus obtaining 21-acetoxy-4,16-pregnene-3,20-dione, m.p. 152.5°–153.5° C.

EXAMPLE 5

250 mg. of 3,3-(2',2'-dimethylethylenedioxy)-5,9(11)-androstadien-17-one is reacted under the conditions set forth in Example 2, thus producing 21-acetoxy-4,9(11),16-pregnatriene-3,20-dione, m.p. 130°–131° C.

EXAMPLE 6

250 mg. of 3β,17β-dihydroxy-21-methoxy-17β-pregn-5-ene-3,20-dione is combined with 20 ml. of anhydrous acetonitrile and 1.2 g. of acetic acid - p-toluenesulfonic acid anhydride and stored for 24 hours at room temperature. The reaction mixture is then poured into water, extracted with chloroform; the chloroform phase is washed, dried, and concentrated under vacuum. The residue is dissolved in 5 ml. of dimethylformamide, combined with 400 mg. of anhydrous potassium acetate, and heated for 6 hours to 105° C. The reaction mixture is worked up as described in Example 3(b), thus obtaining 3β,21-diacetoxy-5,16-pregnadien-20-one, m.p. 149°–151° C. (from acetone-hexane).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of preparing $\Delta^{16}$-21-hydroxy-20-keto steroids of the pregnane series having a 13-methyl or -ethyl group and an otherwise unsubstituted D-ring, and 21-ethers thereof, comprising the steps of
    (a) condensing a corresponding 17-keto steroid containing no other free keto function with a lithium compound of the formula

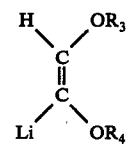

wherein $R_3$ and $R_4$ each are alkyl of 1–4 carbon atoms or collectively are alkylene or alkylidene of 1–3 carbons in the alkylene or alkylidene chain and up to 6 carbon atoms in the alkylene or alkylidene, thereby converting the 17-keto group to a 17β-hydroxy-20α-enol ether in which the 17α-side-chain has the formula

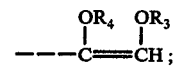

and, in either order,
    (b) hydrolyzing at least the $OR_4$ group of the enol ether thus-produced to form a 20-keto-21-oxy side chain and eliminating the 17β-OH to form a $\Delta^{16}$-double bond.

2. The method of claim 1, wherein $R_3$ and $R_4$ are methyl.

3. The method of claim 1, wherein $R_3$ and $R_4$ collectively are methylene.

4. The method of claim 1, wherein $R_3$ and $R_4$ collectively are dimethylmethylene.

5. The method of claim 1, wherein the $\Delta^{16}$-21-hydroxy steroid is of the formula

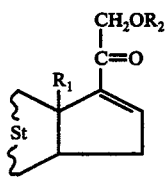

wherein
- $R_1$ is methyl or ethyl;
- $R_2$ is hydrogen alkyl of 1–4 carbon atoms or hydroxyalkyl of 1–4 carbon atoms;
- St is the ABC ring system of a 19-nor-pregnane and is saturated or has 1–4 double bonds or is substituted in the 6- and/or 10-position by methyl and/or in the 3- and/or 11-position by hydroxy, alkoxy of 1–6 carbon atoms, alkanoyloxy of 1–6 carbon atoms, nitriloxy, oxo, alkylenedioxy or alkylidenedioxy of 2–3 carbon atoms in the alkylene which forms a ring with $C_3$ or $C_{11}$ carbons and two oxygen atoms, or phenylenedioxy;
- the 17-keto steroid compound is of the formula

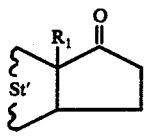

wherein
- $R_1$ is as above and
- St' is the ABC ring system of a 19-nor-pregnane and is saturated or has 1–4 double bonds or is substituted in the 6- and/or 10-position by methyl and/or in the 3- and/or 11-position by hydroxy, alkoxy of 1–6 carbon atoms, alkanoyloxy of 1–6 carbon atoms, nitriloxy, trialkylsilyloxy of 1–4 carbon atoms in each alkyl, tetrahydropyranyloxy, alkylenedioxy or alkylidenedioxy of 2–3 carbon atoms in the alkylene which forms a ring with $C_3$ or $C_{11}$ carbons and two oxygen atoms, or phenylenedioxy;

and the condensation product from said 17-keto steroid compound and the lithium compound is of the structure

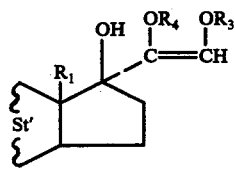

and St', $R_1$, $R_3$ and $R_4$ are as above.

6. The method of claim 5, wherein in step (b) both the $OR_3$ and $OR_4$ groups are hydrolyzed and which comprises the further step of etherifying or esterifying the $C_{21}$-hydroxyl of the thus-produced $\Delta^{16}$-21-hydroxy-20-keto steroid.

7. A compound selected from the group consisting of (a) 19-nor-pregnanes of the formula

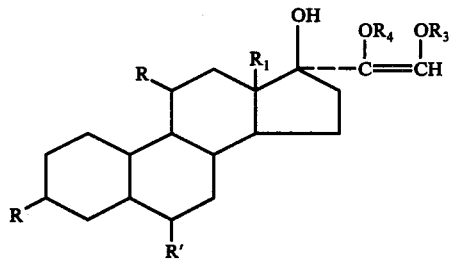

wherein R' is a hydrogen atom or methyl; R is a hydrogen atom or a substituent selected from the group consisting of hydroxy, alkoxy of 1–6 carbon atoms, acyloxy of 1–6 carbon atoms, trialkylsilyloxy of 1–3 carbon atoms in each alkyl group, tetrahydropyranyloxy, alkylenedioxy of 2–6 carbon atoms and forming a 5–6 membered ring and phenylenedioxy; $R_1$ is methyl or ethyl; and $R_3$ and $R_4$ each are alkyl of 1–4 carbon atoms or collectively are alkylene or alkylidene of up to 6 carbon atoms forming a 5 or 6 membered ring; (b) the corresponding 10-methyl-pregnanes, (c) unsaturated pregnanes and 19-nor-pregnanes corresponding to (a) and (b) having a 9(11) double bond; (d) unsaturated pregnanes corresponding to (a), (b) and (c) having, when R at the 3-position is β-hydroxy or ketalized oxo, either a 5(6) or 5(10) double bond; and (e) unsaturated pregnanes corresponding to (a), (b) and (c) having, when R at the 3-position is an esterified or etherified hydroxy, a double bond in the 1,3,5(10)-, 2,5(10)-, 3-, 5- or 3,5-positions.

8. 20,21-dimethoxy-3-(2'-tetrahydropyranyloxy)-17α-pregna-5,20-dion-17β-ol, a compound of claim 7.

9. A process of claim 5 wherein the 17-keto steroid is selected from the group consisting of (a) saturated androstanes of the formula

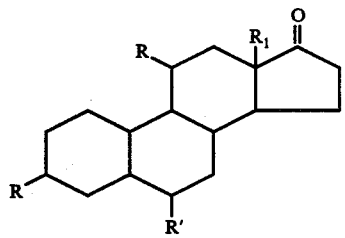

wherein R' is hydrogen or methyl; $R_1$ is methyl or ethyl; and R is a hydrogen atom or a substituent selected from the group consisting of hydroxy, alkoxy of 1–6 carbon atoms, acyloxy of 1–6 carbon atoms, trialkylsilyloxy of 1–3 carbon atoms in each alkyl group, tetrahydropyranyloxy, alkylenedioxy of 2–6 carbon atoms and forming a 5–6 membered ring and phenylenedioxy; (b) the corresponding androstanes having a methyl group at the 10-position; (c) unsaturated androstanes corresponding to (a) and (b) having a 9(11) double bond; (d) unsaturated androstanes corresponding to (a), (b) and (c) having, when R at the 3-position is β-hydroxy or ketalized oxo, either a 5(6) or 5(10) double bond; and (e) unsaturated androstanes corresponding to (a), (b) and (c) having, when R at the 3-position is an esterified or etherified hydroxy, a double bond in the 1,3,5(10)-, 2,5(10)-, 3-, 5- or 3,5-position.

* * * * *